United States Patent
Haveri

(10) Patent No.: US 9,492,106 B2
(45) Date of Patent: Nov. 15, 2016

(54) RESPIRATORY SENSOR

(75) Inventor: Heikki Haveri, Huhmari (FI)

(73) Assignee: GENERAL ELECTRIC COMPANY, Schenectady, NY (US)

(*) Notice: Subject to any disclaimer, the term of this patent is extended or adjusted under 35 U.S.C. 154(b) by 784 days.

(21) Appl. No.: 12/711,741

(22) Filed: Feb. 24, 2010

(65) Prior Publication Data

US 2011/0046500 A1    Feb. 24, 2011

(30) Foreign Application Priority Data

Apr. 3, 2009 (EP) .................................. 09396005

(51) Int. Cl.
*A61B 5/08* (2006.01)
*A61B 5/087* (2006.01)
*A61B 5/00* (2006.01)
*A61B 5/097* (2006.01)

(52) U.S. Cl.
CPC ........... *A61B 5/0878* (2013.01); *A61B 5/4818* (2013.01); *A61B 5/097* (2013.01)

(58) Field of Classification Search
CPC ... A61B 5/0878; A61B 5/4818; A61B 5/097
USPC ................................................ 600/529–543
See application file for complete search history.

(56) References Cited

U.S. PATENT DOCUMENTS

| 5,069,222 A | 12/1991 | McDonald, Jr. |
| 5,195,529 A | 3/1993 | Malkamaki |
| 7,087,027 B2 | 8/2006 | Page |
| 2007/0093724 A1 | 4/2007 | Nakano |
| 2007/0125380 A1* | 6/2007 | Acker et al. ............. 128/204.23 |
| 2009/0069646 A1 | 3/2009 | Yamamori et al. |
| 2010/0113956 A1* | 5/2010 | Curti et al. ................... 600/538 |

FOREIGN PATENT DOCUMENTS

| EP | 0604564 B1 | 4/1998 |
| EP | 1044037 B1 | 4/2006 |
| FI | 79240 A | 5/1988 |
| FI | 890669 A | 8/1989 |
| FI | 84693 B | 9/1991 |
| WO | 9114469 A | 10/1991 |
| WO | 2006138580 A | 12/2006 |

OTHER PUBLICATIONS

SleepStrip Sleep Apnea Sensor and SleepSense Sleep Lab Sensors for Latin America http://www.biosafepanama.com/html/sleepstrip.html.

* cited by examiner

*Primary Examiner* — Tiffany Weston
(74) *Attorney, Agent, or Firm* — GE Global Patent Operation; Marc. A. Vivenzio

(57) ABSTRACT

A sensor for measuring a respiration is disclosed herein. The sensor includes at least one housing (7) having a first cavity (12) with a first port (11) allowing a respiration gas flow, and a second cavity (22) with a second port (21) also allowing a respiration gas flow. The sensor also includes at least one breathing detector (51) for acquiring a signal indicative of the respiration gas flowing through the first cavity and the second cavity. The at least one housing is equipped with at least one additional port (31) for removing the respiration gas flow coming from the first cavity and the second cavity, which additional port being separate from the first port and the second port.

14 Claims, 2 Drawing Sheets

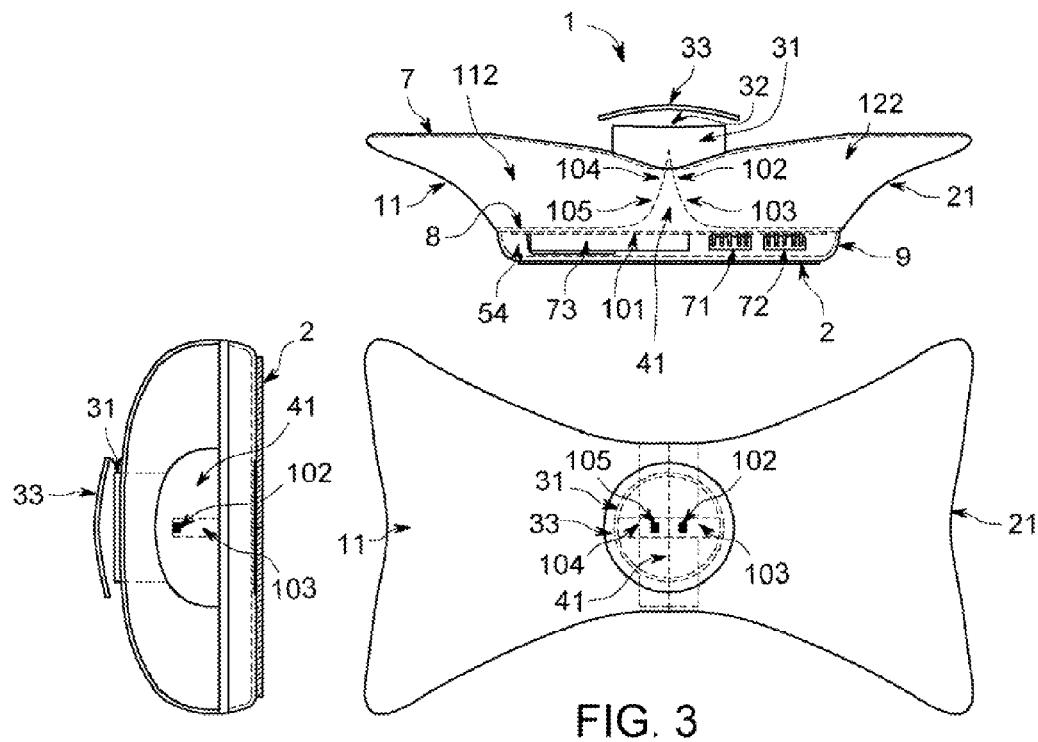
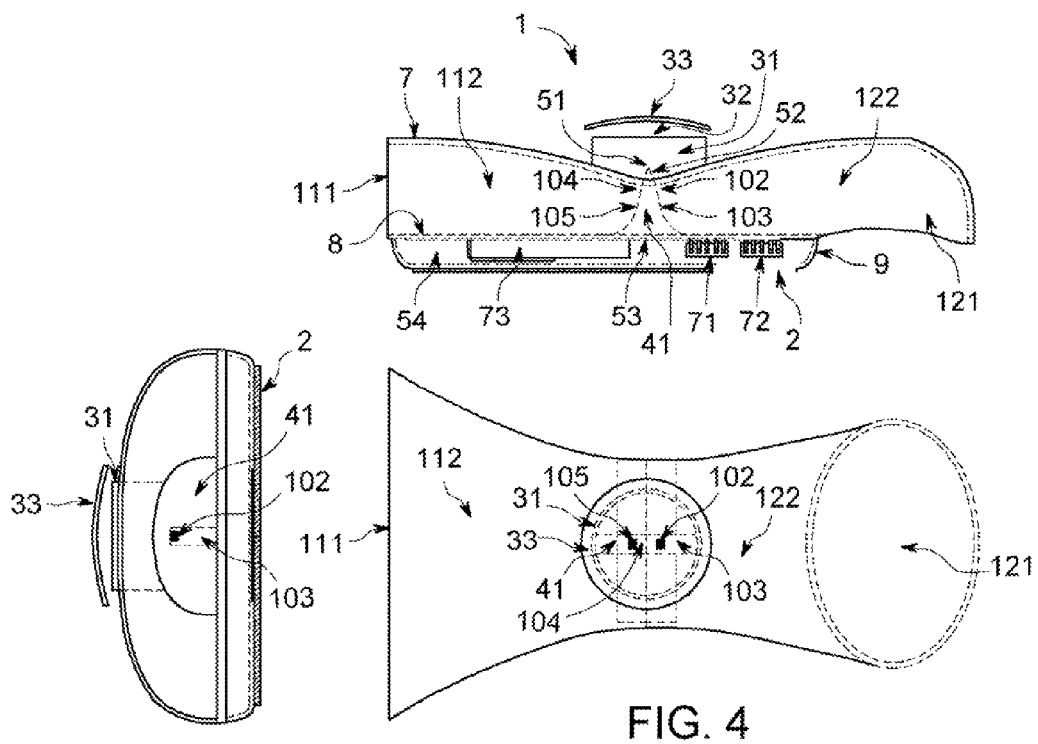

RESPIRATORY SENSOR

CROSS-REFERENCE TO RELATED APPLICATIONS

This application claims priority under 35 U.S.C. §119 (a)-(d) or (f) to prior-filed, co-pending European patent application serial No. 09396005.2, filed on Apr. 3, 2009, which is hereby incorporated by reference in its entirety.

BACKGROUND OF THE INVENTION

This disclosure relates generally to a sensor for measuring a respiration.

During apnea there is no movement of the muscles of respiration and the volume of the lungs initially remains unchanged. Depending on the openness of the airways there may not be a flow of breathing gas between the lungs and the ambient during apnea. Apnea can be drug-induced (e.g., opiate toxicity), mechanically induced (e.g., strangulation or choking), or it can occur as a consequence of neurological disease or trauma as was explained above.

Many people in hospital wards suffer from apnea, caused by opiates or other medicine. Patients may also have obstructive apnea, which is caused by a blockage in the airways, such as thong or similar physical obstruction. Patients usually don't have any monitoring connected on as it is rather expensive and there are usually many patients in the ward. Furthermore, there is also shortage of nursing personnel keeping an eye on patients continuously.

Many healthy people suffer from sleep apnea that can be divided into three distinct forms: central, obstructive, and a complex sleep apnea, which is a combination of central and obstructive apnea. In central sleep apnea, breathing is interrupted by the lack of respiratory effort. In obstructive sleep apnea, breathing is interrupted by a physical block to airflow despite respiratory effort. In complex sleep apnea, there is a transition from central to obstructive features during the events themselves. Central apnea is commonly caused by neurological etc. characteristics, whereas obstructive apnea is caused by for example over weight.

Many elderly people at home have to take lot of different medical pills or other type of medicine, which may cause apnea. Also many infants, small babies and even small children up to three years age suffer from sudden infant death syndrome (SIDS). It is also very stress full for many parents, as they can not sleep well during nights, since they compulsively wake up to see how their small babies and children are sleeping.

Currently there does not exist a device that can reliably measure the actual breathing gas flow through the nose or the mouth and can reliably detect apnea. The standard definition of apnea is cessation of inspiratory gas flow for 20 seconds, or for a shorter period of time if accompanied by bradycardia (heart rate less than 100 beats per minute), cyanosis, or pallor. Most devices, such as impedance measurement, resistive belts, or piezo-resistive belts etc., does not measure the actual flow of breathing gas through the nose or the mouth, but they measure for example the respiratory muscle movement or chest movement. These indirect measurements are unreliable since the respiratory muscle or chest movement may occur even when the patient is suffering from apnea. Devices are also sensitive to motion artefacts and other disturbances. Some devices try to measure the actual breathing gas flow through the nose or the mouth. Devices, based on sensing the breathing gas flow or the pressure, are very sensitive to mechanical motion and vibrations as well as surrounding air flowing by, causing disturbances and artefacts. Devices based on measuring the thermal flow of breathing gas are less sensitive to motion, but they are very sensitive to surrounding air flowing by the device that causes signal disturbances and artifacts. Some of them are also very sensitive to false skin contact that decreases the sensitivity or even destroy the measurement.

Disposability is one of the clinical requirements for the device that is in close contact to patient's airways, since existing cleaning practices are not reliable enough to ensure high enough level of purity for reusable devices. Contaminated reusable devices easily cause a risk of cross contamination between different patients, who already have a lowered level of immunity against bacteria and viruses. Existing devices are rather expensive and thus they are usually reusable.

Existing apnea sensors based on measuring the thermal flow of the breathing gas usually contain two or three thermistors. It is common to place two thermistors into both hawse pipes and one in to the front of the mouth. Some devices have one thermistor placed under the nose and one in front of the mouth. In most of the devices thermistors are suspended in to open air and they are in straight connection with interfering air flowing by the thermistors or thermistors may even be in straight contact with patient's skin. Such devices suffer from signal disturbances and lowered or no signal sensitivity as the thermal mass is increased by the patient's body. Some devices may have housing covering the thermistors to minimize signal disturbances caused by the flowing surrounding air or skin contact. However, the housing forms a continuous cavity between the mouth and the nose also connecting the thermistors into one common gas flow path. When the patient breathes through the nose and the mouth at the same time, there is no gas flow through the cavity and no gas flow by the thermistors. Obviously, the measurement signal would be zero or something that is not proportional to respiration flow and respiration rate. When the patient breaths through the nose or the mouth the same air flows back and forth in the channel causing flow disturbances and error to the measurement and in the worst case it decreases the patient safety as the patient re-breaths gases, which causes decreased gas exchange in the lungs.

BRIEF DESCRIPTION OF THE INVENTION

The above-mentioned shortcomings, disadvantages and problems are addressed herein which will be understood by reading and understanding the following specification.

In an embodiment, a sensor for measuring a respiration includes at least one housing having a first cavity with a first port allowing a respiration gas flow, and a second cavity with a second port also allowing a respiration gas flow. The sensor for measuring the respiration also includes at least one breathing detector for acquiring a signal indicative of the respiration gas flowing through the first cavity and the second cavity. The at least one housing is equipped with at least one additional port for removing the respiration gas flow coming from the first cavity and the second cavity, which additional port being separate from the first port and the second port.

In another embodiment, s sensor for measuring a respiration includes at least one housing having a first cavity with a first port allowing a respiration gas flow, and a second cavity with a second port also allowing a respiration gas flow. The sensor for measuring the respiration also includes at least one breathing detector for acquiring a signal indicative of the respiration gas flowing through the first cavity and the second cavity and an electronic circuit board for processing the signal and being in contact with the at least one breathing detector. The at least one housing is equipped with at least one additional port for removing the respiration gas coming from the first cavity and the second cavity, which additional port being separate from the first port and the second port.

In yet another embodiment, a sensor for measuring a respiration includes at least one housing having a first cavity with a first port allowing a respiration gas flow, and a second cavity with a second port also allowing a respiration gas flow. The sensor for measuring the respiration also includes at least one breathing detector for acquiring a signal indicative of a flow rate of the respiration gas flowing through the first cavity and the second cavity. The at least one housing is equipped with at least one additional port for removing the respiration gas coming from the first cavity and the second cavity, which additional port is separate from the first port and the second port and which additional port is covered with a hood to prevent disturbing ambient airflows to enter the additional port.

Various other features, objects, and advantages of the invention will be made apparent to those skilled in art from the accompanying drawings and detailed description thereof.

BRIEF DESCRIPTION OF THE DRAWINGS

FIG. 3 is a cross sectional view of a second embodiment of the respiration sensor from three different projections; and FIG. 4 is a cross sectional view of a third embodiment of the respiration sensor from three different projections.

DETAILED DESCRIPTION OF THE INVENTION

Figure 1:
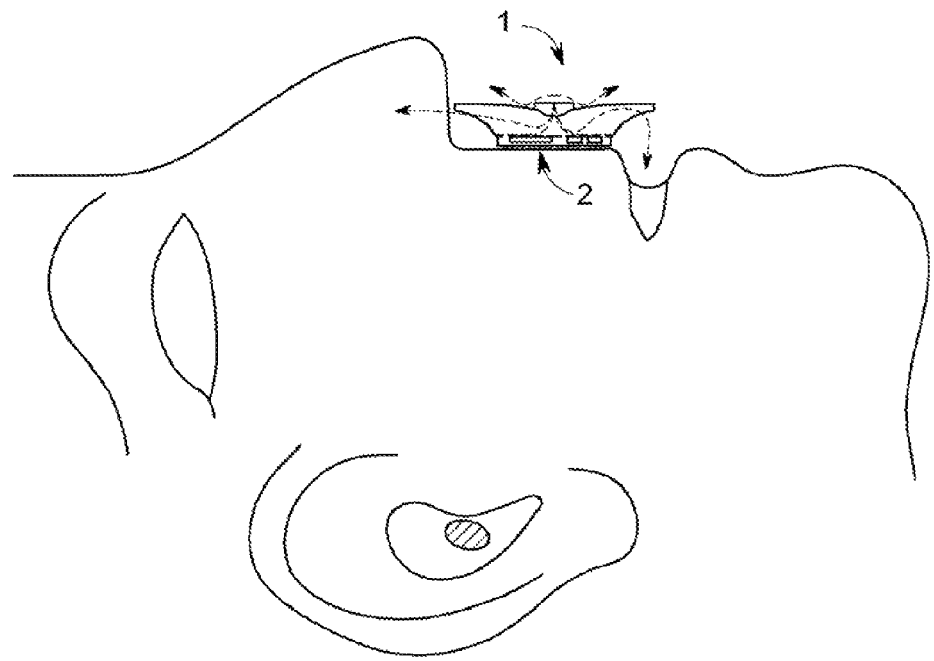
FIG. 1 is a side view of the respiration sensor connected to a subject.
Figure 2:
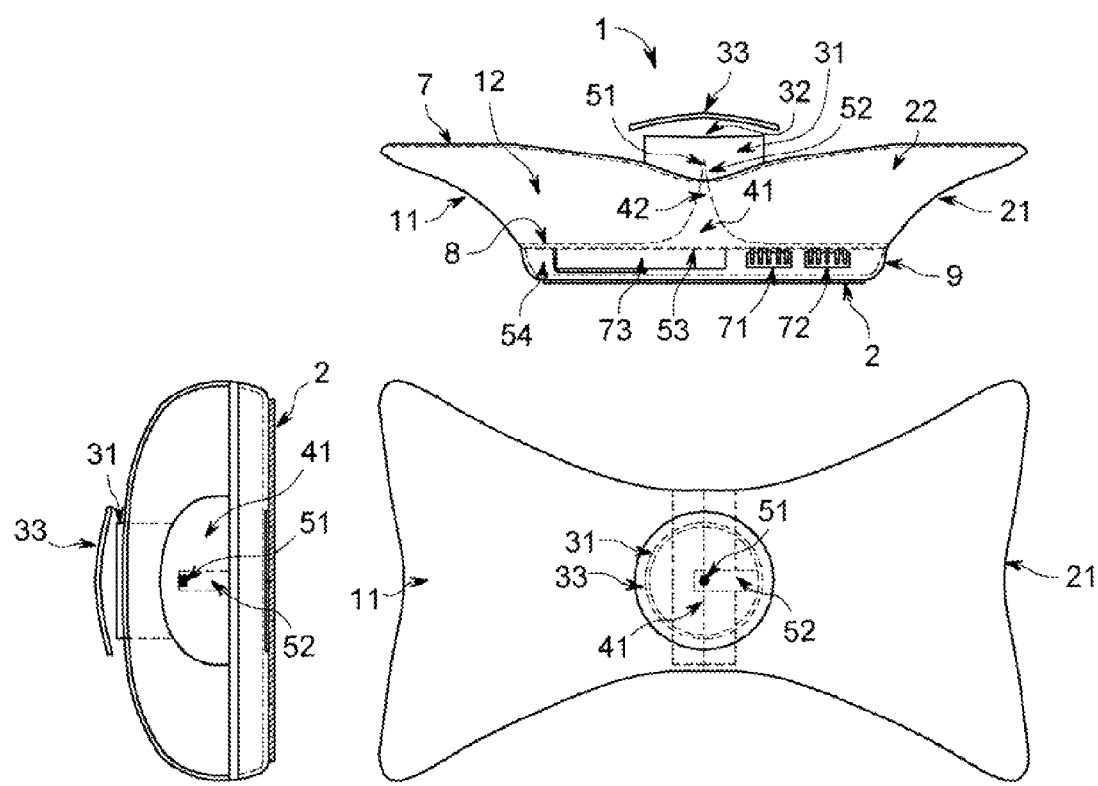
FIG. 2 is a cross sectional view of the respiration sensor from three different projections.

FIG. 1 shows a sensor 1 for measuring a respiration which is substantially insensitive to any motion or mechanical vibrations. The sensor 1 can be used to acquire a signal indicative of a flow or a relative flow or a respiration rate of a respiration gas flow through a nose, a mouth or the both at the same time and can also detect apnea. The measurement is based on measuring a thermal component of the respiration gas flow with at least one breathing detector 51 such as a thermistor as shown in FIG. 2. Thermal changes of the respiration gas flowing by the thermistor change the breathing detector's resistance, which is converted into a continuous electrical signal. The amplitude of the signal is proportional to the flow rate of the breathing gas and the frequency is proportional to the respiration rate (RR). These signals can also be used for detecting apnea. Also it is possible to use the breathing detector 51 to acquire a signal indicative of one or more component or their concentration in the respiration gas.

The sensor 1 for measuring the respiration is placed on a skin below a nose but above the subject's upper lip or mouth, where it is glued on with a sticker 2 located on the bottom of the sensor 1.

FIG. 2 shows three different projections of the sensor 1 for measuring the respiration. The sensor 1 comprises a first port 11 opening towards the nose, a second port 21 opening towards the mouth and at least one additional port 31, located between the first port 11 and the second port 21 and it preferably opens away from the subject. The sticker 2 is in this embodiment opposite to the opening direction of the additional port 31. The first ports 11 and the second port 21 have symmetrical construction relative to the additional port 31 so that the sensor 1 can be placed either way between the nose and the mouth. The first port 11 and the second port 21 connect to the additional port 31 through continuous cavities, at least one housing 7 surrounding a first cavity 12 and a second cavity 22, where the respiratory air can flow between the subject's respiratory system and the ambient. Thus the first port 11 allows the respiration gas flow into the first cavity 12 and the second port 21 allows the respiration gas flow into the second cavity 22 in case the additional port 31 is only removing the respiration gas and correspondingly the first port 11 allows only the respiration gas flow out from the first cavity 12 and the second port 21 allows only the respiration gas flow out from the second cavity 22 in case the additional port 31 is allowing the respiration gas flow into the first cavity 12 and the second cavity 22. Instead of using one additional port 31 there may be two or more additional ports, one for the first cavity 12 and another for the second cavity 22.

As shown in FIG. 2 the first cavity 12 and the second cavity 22 are against one another. The first cavity 12, extending from the nose to the additional port 31, is for the respiratory gas flowing between the nose and the ambient as shown with dashed lines in FIG. 1, whereas the second cavity 22, extending from the mouth to the additional port 31, is for the respiratory gas flowing between the mouth and the ambient as also shown with dashed lines in FIG. 1. Inside the sensor 1, in a cross section of cavities 12, 22, on a bottom plate 8, in the middle of the additional port 31, is a flow guide 41 that directs the gas flow from either of the cavities 12 and/or 22 towards an opening 32 of the additional port 31 or vice versa. The flow guide 41 turns the respiration gas flow direction of the first cavity and the second cavity meaning that also the first cavity and the second cavity are turned 30-90 degrees, more specifically 45-90 degrees, or even more specifically 80-90 degrees to achieve the at least one additional port 31. Furthermore the flow guide 41 prevents the respiration gas to flow between the cavities 12 and 22, in other words between the nose and the mouth, that would otherwise cause subject to re-breath gases and decrease the gas exchange in the lungs.

The at least one breathing detector 51 is placed on the at least one additional port 31 or is close by the additional port 31. In the embodiment shown in FIG. 2 only one breathing detector 51 is enough, but naturally there can be more than one. The breathing detector 51 can be fixed on a strip 52 branching from a flexible electronic circuit board 53, which is located inside an intermediate space 54 formed between the bottom plate 8 and a lower housing 9. The housings 7 and 9, as well as the bottom plate 8 are preferably made of recyclable plastic or similar material that can be easily and inexpensively produced, has low unecological impact and has a low thermal conductivity to achieve a good measurement sensitiveness. The strip 52 extends through an opening in the bottom plate 8, from the intermediate space 54, into one of the first cavity 12 and the second cavity 22 as shown in FIG. 2 and bends against the flow guide 41, so that the breathing detector 51 is located close into the middle of the tip 42 of the flow guide 41, in to the middle of the gas flow directed by the flow guide 41 inside the additional port 31.

The breathing detector 51, which may be the thermistor, senses the thermal component of the respiratory gas flowing past the breathing detector 51, between the respiratory system and the ambient, which changes the breathing detector 51 resistance proportional to the temperature change of the flowing gas, which is then transformed into a continuous electrical signal. When the subject breathes out the warm breathing gas coming from the respiratory system warms up the breathing detector 51 increasing/decreasing the resistance of PTC/NTC type breathing detector, whereas the subject breathes in the cooler air from the ambient it cools down the breathing detector decreasing/increasing the resistance of PTC/NTC type breathing detector. The thermal connection between the breathing detector 51 and the surrounding mechanics has to be low to ensure high sensitivity and fast response time to temperature changes caused by the flowing respiratory air. To increase the sensitiveness, the cross sectional shape of the first cavity 12 and the second cavity 22 decrease from the openings of first port 11 and the second port 21 towards the flow guide 41 and the additional port 31. A cross-sectional area of the at least one additional port 31 may be less than 10% of a combined cross-sectional area of the first port 11 and the second port 21, more specifically less than 20% or even more specifically less than 50% of the combined cross-sectional area of the first port and the second port. This increases the flow speed of respiratory gas along the first cavity 12 and the second cavity 22 to its maximum speed as it enters the additional port 31 and passes the breathing detector 51 placed close to the narrowest cross sectional area of the whole respiratory gas flow bath. The increased speed of the respiratory gas flow increases the heating/cooling effect of the gas flowing past the breathing detector 51 in turn increasing the sensitiveness of the respiratory gas flow measurement.

The additional port 31 is covered with a hood 33, or a similar protective construction, to prevent any disturbing ambient airflows, such as airflow from the air conditioner etc., to enter straight in to the additional port 31 and to the breathing detector 51 that may cause error or even destroy the measurement of respiratory gas flow.

The breathing detector 51 electrically connects to the electronics located on the bottom side of the flexible electronic circuit board 53 inside the intermediate space 54. The electronics comprise an amplifier 71 for amplifying the voltage signal from the breathing detector 51, a processor 72 for converting the amplified analog voltage signal into a digital form and for processing the digital data into values of RR and real time waveform data. The processor 72 may even comprise radio frequency transceiver, or similar, for wireless communication between the host device, such as patient monitor (not shown in Figure) that could show the real time waveform and the value of RR, as well as apnea and other alarms on its display. The operating power for the wireless respiration sensor 1, as described previously, can be delivered from an electrical battery 73, such as 3V, Li-battery made by the company Varta Consumer Batteries, which diameter is 12.5 mm and the height is 1.6 mm.

It is obvious that the sensor 1 can be connected to the patient monitor or similar host through electrical cable as well (not shown in Figure). In this case it is reasonable to leave out most of the electronics and the electrical battery, such as processor etc. from the respiration sensor and place them into the host device.

In the sleep laboratory, where subjects suffering from different type of sleep apnea are examined, it is sometimes important to know if the subject is breathing through the nose or the mouth. FIG. 3 shows a respiration sensor, which is slightly modified from the sensor shown in FIG. 2, comprising a alternative electronic flex circuit board 101. In the circuit 101, the breathing detector 102 is placed on a strip 103 that bends against the wall of the flow guide 41 extending only on the side of the wall. The breathing detector 102 can only acquire a signal indicative of the respiration gas flowing through the second cavity 122 which signal is in this specific case the thermal component of the respiratory gas flow between the mouth and the ambient. Similarly, the breathing detector 104 is placed on a strip 105 that bends against the wall on the adjacent side of the flow guide 41 in regard to the breathing detector 102, also extending only on the side of the wall. The breathing detector 104 can only acquire a signal indicative of the respiration gas flowing through the first cavity 112 which signal is in this specific case the thermal component of the respiratory gas flow between the nose and the ambient. In this embodiment the housing 7 is equipped with two additional ports 31 and both additional ports are equipped with the breathing detector 102, 104, one breathing detector 104 acquiring the signal indicative of the respiration gas coming from the nose or to the nose along the first cavity 112 and another breathing detector 102 acquiring the signal indicative of the respiration gas coming from the mouth or to the mouth along the second cavity 122 This construction increases the cost of the disposable respiration sensor compared to the construction shown in FIG. 2, but it enables the measurement of thermal components of respiratory gas flows between the mouth and the ambient as well as the nose and the ambient separately.

The construction of the sensor 1 described above and shown in FIGS. 2 and 3 is position sensitive and can be positioned either way in regard to the nose and the mouth, whereas it is desirable to be placed only one way to get correct flow data from the nose and the mouth. To help the right positioning, the sensor 1 may have pictures or text on the top surface of the housing 7 showing the user, which way the sensor should be placed in regard to the nose and the mouth. However, there still remains a high possibility for user errors that the respiration sensor is positioned incorrectly, which in turn causes the flow data to be mixed crosswise between the nose and the mouth.

FIG. 4 shows a further embodiment, which solves the problem described above and shown in FIG. 3. The construction is almost the same as in the FIG. 3, except the port 121 towards the mouth is a trough-like guide having a shape of a spoon or similar. The spoon like second port 121 efficiently directs the respiratory gas flow from the mouth towards the second cavity 122, where it continues to flow out from the additional port 31. Similarly, the first port 111 towards the nose has a straight opening that efficiently directs the respiratory gas flow from the nose towards the first cavity 112, continuing the flow out through the additional port 31. With this construction it is safe to mate the breathing detector 104 with the first port 111 for measuring the respiratory gas flow between the nose and the ambient and similarly to mate the breathing detector 102 with the second port 121 for measuring the respiratory gas flow between the mouth and the ambient since, if the respiration sensor is placed on the subject's upper lip so that the first port 111 is towards the mouth, the opening of the second port 121 is closed by the upper lip. This prevents the respiratory gas to flow between the nose and the ambient, when the respiration sensor is placed incorrectly, causing the respiration sensor to show zero or a constant value, which in turn can be alarmed for the user.

The breathing detector 51 may comprise a gas analyzer measuring, for example the gas component or the gas concentration of $CO_2$ or $O_2$ from the breathing gas, or similar. However, the size of the gas analyzer has to be small enough to fit the construction and to be unnoticeable for the subject. Chemical cells, gas absorption at infrared wavelengths etc. are potential technologies already available to fit the sensor 1.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A sensor for measuring a respiration comprising:
   at least one housing defining a first cavity with a first port configured for receiving a respiration gas flow exiting a patient's nose, and a second cavity with a second port, the second port configured for receiving a respiration gas flow exiting the patient's mouth;
   at least one additional port located between the first port and the second port for receiving the respiration gas flow exiting from said first cavity and said second cavity and opening to ambient air, said additional port being separate from said first port and said second port;
   a flow guide positioned in the middle of the additional port and between the first cavity and the second cavity for preventing respiration gas flow between the first cavity and the second cavity; and
   at least one breathing detector disposed proximate said additional port for acquiring a signal indicative of a thermal component of the respiration gas exiting, at least one of said first and second cavity.

2. The sensor according to claim 1, wherein a cross-sectional area of said at least one additional port is less than 10% of a combined cross-sectional area of said first port and said second port, more specifically less than 20% or even more specifically less than 50% of the combined cross-sectional area of said first port and said second port.

3. The sensor according to claim 1, wherein said first cavity and said second cavity are adjacent one another.

4. The sensor according to claim 1, wherein the flow guide is configured for guiding the respiration gas out from said first cavity and said second cavity through said at least one additional port.

5. The sensor according to claim 4, wherein said flow guide is configured to turn the respiration gas flow direction of said first cavity and said second cavity in a range between 30-90 degrees.

6. The sensor according to claim 1, wherein said breathing detector acquiring the signal indicative of the respiration gas flow is configured to be located at said at least one additional port.

7. The sensor according to claim 1, wherein said at least one additional port comprises two additional ports, one for said first cavity and another for said second cavity.

8. The sensor according to claim 7, wherein the breathing detector comprises two breathing detectors, one each being configured for sensing a thermal component of the respiration gas exiting the first and second cavities, respectively.

9. The sensor according to claim 1 further comprising a sticker for placing said housing on a skin of a subject below a nose but above an upper lip.

10. The sensor according to claim 1 wherein the breathing detector is positionable for acquiring a signal indicative of a thermal component of the respiration gas exiting only the first cavity.

11. The sensor according to claim 1 wherein the breathing detector is positionable for acquiring a signal indicative of a thermal component of the respiration gas exiting only the second cavity.

12. The sensor according to claim 1 wherein the breathing detector is positionable for acquiring a signal indicative of a thermal component of the respiration gas exiting both of the first cavity and the second cavity.

13. The sensor according to claim 1, the sensor being positionable so that said first cavity is configured to receive the respiration gas coining from a patient's nose and said second cavity is configured to receive the respiration has coming from the patient's mouth.

14. The sensor according to claim 1, wherein the first port and the second port have symmetrical construction so that the sensor can be positioned with either of the first or second port adjacent the patient's nose and the other of the first and second port adjacent the patient's mouth.

* * * * *